(12) United States Patent
Kim et al.

(10) Patent No.: US 7,348,402 B2
(45) Date of Patent: Mar. 25, 2008

(54) ANTIMICROBIAL PEPTIDE, ITS ANALOGS AND ANTIMICROBIAL COMPOSITION COMPRISING THEM

(75) Inventors: Sun-Chang Kim, Daejeon (KR); In-Yup Park, Seongnam (KR); Ju-Hyun Cho, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 403 days.

(21) Appl. No.: 10/509,366

(22) PCT Filed: Mar. 26, 2003

(86) PCT No.: PCT/KR03/00602

§ 371 (c)(1), (2), (4) Date: Sep. 24, 2004

(87) PCT Pub. No.: WO03/080652

PCT Pub. Date: Oct. 2, 2003

(65) Prior Publication Data

US 2005/0215481 A1   Sep. 29, 2005

(30) Foreign Application Priority Data

Mar. 26, 2002   (KR) .................. 10-2002-0016445

(51) Int. Cl.
*C07K 14/00* (2006.01)
*A61K 38/00* (2006.01)

(52) U.S. Cl. .............. 530/327; 530/326; 530/300; 514/2; 514/13; 514/14

(58) Field of Classification Search ............ 530/327, 530/326, 300; 514/2, 13, 14
See application file for complete search history.

(56) References Cited

U.S. PATENT DOCUMENTS 5,607,914 A   3/1997   Rao et al.
5,830,993 A   11/1998  Blecha et al.
5,936,063 A * 8/1999   Kim et al. .............. 530/324
2003/0148397 A1* 8/2003  Leite et al. ............. 435/7.4

FOREIGN PATENT DOCUMENTS

| JP | 8-143596 A1 | 6/1996 |
|---|---|---|
| JP | 9-165342 A1 | 6/1997 |
| WO | WO-99/26971 A1 | 6/1999 |
| WO | WO 99/37664 * | 7/1999 |

OTHER PUBLICATIONS

Park et al. Structure-activity analysis of buforin II, a histone H2A-derived antimicrobial peptide: The proline hinge is responsible for the cell-penetrating ability of buforin II. Jul. 18, 2000, proceedings of the National Academy of Science, USA, vol. 97, No. 15, pp. 8245-8250.*
Park et al. Mechanism of Action of the Antimicrobial Peptide Buforin II: Bofurin II Kills Microorganisms by Penetrating the Cell Membrane and Inhibiting Cellular Functions. 1998, Biochemica and Biophysical research Communications, vol. 244, pp. 253-257.*
Park et al. helix Stability Confers Salt Resistance upon Helical Antimicrobial Peptides. Apr. 2, 2004, The Journal of Biological Chemistry, vol. 279, No. 14, pp. 13896-13901.*
Chan Bae Park et al., "A Novel Antimicrobial Peptide from Bufo bufo gargarizans", Biochemical and Biophysical Research Communications 218, 408-413 (1996).
Michael Zasloff "Magainins, a class of antimicrobial peptides from *Xenopus* skin: Isolation, characterization of two active forms, and partial cDNA sequence of a precursor", Proc. Natl. Acad. Sci., USA vol. 84, Aug. 1987, 5449-5453.

* cited by examiner

*Primary Examiner*—Jon Weber
*Assistant Examiner*—Abdel A Mohamed
(74) *Attorney, Agent, or Firm*—Darby & Darby P.C.

(57) ABSTRACT

Disclosed is a novel antimicrobial peptide having excellent antimicrobial activities, its analogs and an antimicrobial composition comprising them. The antimicrobial peptide alternatively comprises basic amino acid residues and hydrophobic amino acid residues, and is able to penetrate into microbial cells and act against a wide variety of microorganisms.

12 Claims, 2 Drawing Sheets

ANTIMICROBIAL PEPTIDE, ITS ANALOGS AND ANTIMICROBIAL COMPOSITION COMPRISING THEM

This application is the U.S. national stage filing of International Patent Application No. PCT/KR03/000602, filed Mar. 26, 2003, published in WO 99/37664 on Jul. 29, 1999, which claims the priority of Republic of Korea Patent Application No. 16445/2002, filed on Mar. 26, 2002, both of which are incorporated by reference herein in their entireties.

TECHNICAL FIELD

The present invention relates to antimicrobial peptides. More particularly, the present invention relates to novel peptides exhibiting strong antimicrobial activities against a wide variety of microorganisms including bacteria and fungi; analogs thereof; and antimicrobial composition comprising them.

BACKGROUND ART

After discovering a new antimicrobial peptide, cecropin from the silkworm larva as a result of a defense-mechanism in insects against invasion of microorganisms, peptides have begun to be recognized as important biologically active materials. Recent studies show that most of the higher living things accumulate in or secrete into their bodies antimicrobial peptides as a defense-mechanism against pathogens, independently from the immune system. More than 2,000 antimicrobial peptides have been discovered up to date. These peptides found in different species have different amino acid compositions, but the mechanisms of antimicrobial activity are similar to one another.

The most widely known antimicrobial peptides include cecropin, magainin, bombinin, defensin, tachyplesin and buforin. These antimicrobial peptides are composed of 17-24 amino acids, and have antimicrobial activity against Gram-negative and Gram-positive bacteria as well as protozoa and fungi. Some of these peptides show anti-cancer or anti-viral activity. Especially, magainin is a peptide with 23 amino acids separated from the epidermis of amphibians (Zasloff, M. (1987) *Proc. Natl. Acad. Sci. USA*, 84:5449-5453) and can act against human lung cancer cells as well as pathogens. Also, most of the antimicrobial peptides act and kill the target cells specifically and promptly, and exhibit activity spectrum against a wide range of microorganisms (Park, C. B., Kim, M. S. and Kim, S. C. (1996) *Biochem. Biophys. Res. Comm.* 218:408-413).

The above antimicrobial peptides
1. have strong antimicrobial activity against a wide variety of microorganisms,
2. are not toxic to human body since they do not destroy host cells, but act specifically against extraneous pathogens,
3. have little possibility to cause resistance since they show antimicrobial activity by totally different mechanisms from conventional antimicrobial drugs causing resistance,
4. can be mass produced by genetic modification since they do not undergo secondary modification such as glycosylation, and
5. have high commercial value in pharmaceutical and food industries since they are physico-chemically stable against heat, acid or alkali.

The action mechanism of antimicrobial peptides reported up to now can be categorized into two, as follows;

First, most of the antimicrobial peptides have an action mechanism of destroying membrane potential by increasing cell membrane permeability and stopping the cellular metabolism. Currently, numerous research results are being reported on the biochemical and structural characteristics of the antimicrobial peptides exhibiting the above action mechanism.

Second, a small number of antimicrobial peptides are able to penetrate into microbial cells and strongly act against the microorganisms by combining with DNA or RNA and prohibiting transcription or translation, but the mechanism of this strong antimicrobial activity, is not being investigated. However, since antimicrobial drugs with new action mechanism are developed actively due to the emergence of microorganisms that are resistant to antimicrobial drugs, it is important to understand the action mechanism of the antimicrobial peptides that is able to penetrate into microbial cells and act against the microorganisms, and it is also important to develop these antimicrobial peptides.

The salient structural features known to be important in the activity of the antimicrobial peptides that is able to penetrate into microbial cells and act against the microorganisms include,
1. amphipathic helix
2. distribution of residues stabilizing the above helix,
3. distribution of basic residues,
4. distribution of hydrophobic residues,
5. dipole interaction between charged residues and amphipathic helix, and
6. salt-bridge between the residues with different charges.

Noticing the above observations, the present inventors have perfected the present invention by synthesizing new antimicrobial peptides, having amino acid residues of these peptides substituted, added or deleted, and then selecting repeatedly the peptide analogs which is able to penetrate into microbial cells and act against the microorganisms.

SUMMARY OF THE INVENTION

The object of the present invention is to provide novel peptides and analogs thereof exhibiting antimicrobial activity against even the microorganisms which are resistant to the traditional antimicrobial peptides, by penetrating into microbial cells and acting against the microorganisms, and an antimicrobial composition comprising them. Also the antimicrobial peptides according to the present invention are novel peptides that have strong antimicrobial activity against a wide variety of microorganisms and negligible or no toxicity when compared to the conventional antimicrobial peptides.

DETAILED DESCRIPTION OF THE INVENTION

The present invention relates to novel peptides having antimicrobial activities. More particularly, the present invention relates to novel peptides and analogs thereof exhibiting strong antimicrobial activity against a wide variety of microorganisms including bacteria and fungi, by penetrating into microbial cells and acting against the microorganisms, and antimicrobial composition comprising them.

The sequence of the amino acids in the present invention was written by using the acronyms according to the nomenclature of IUPAC-IUB.

| | | | |
|---|---|---|---|
| alanine | A | arginine | R |
| asparagines | N | aspartic acid | D |
| cysteine | C | glutamic acid | E |
| glutamine | Q | glycine | G |
| histidine | H | isoleucine | I |
| leucine | L | lysine | K |
| methionine | M | phenylalanine | F |
| proline | P | serine | S |
| threonine | T | tryptophane | W |
| tyrosine | Y | valine | V |

The antimicrobial peptide according to the present invention comprises a central fragment with a relatively conserved amino acid sequence and alternating basic amino acid residues and hydrophobic amino acid residues at the N-terminus and C-terminus sides of the above central fragment. Thereby, the secondary structure of the total peptide is stabilized and the peptide is able to penetrate into microbial cells and act against the microorganisms.

The above hydrophobic amino acid can be selected from any hydrophobic amino acids, and preferably from the group consisting of alanine, valine, leucine, and isoleucine. The above basic amino acid can be selected from any basic amino acids, and preferably from the group consisting of lysine, arginine and histidine.

The present invention provides antimicrobial peptide analogs including tides whose sequence is represented by the following sequence equation (I):

$$[\text{N-terminus-}X^1X^2X^3X^4X^5X^6X^7X^8X^9X^{10}X^{11}X^{12}X^{13}X^{14}X^{15}\text{-C-terminus}] \quad (I)$$

$$\underbrace{\phantom{XXXXXXXX}}_{\text{central fragment}}$$

wherein,
$X^1$ is absent or a basic amino acid;
$X^2$ are two identical or different hydrophobic amino acids;
$X^3$ is a basic amino acid;
$X^4$ is glutamine or asparagine;
$X^5$ is phenylalanine or tryptophane;
$X^6$ is proline;
$X^7$ is isoleucine or valine;
$X^8$ is glycine;
$X^9$ is a basic amino acid;
$X^{10}$ are two identical or different hydrophobic amino acids;
$X^{11}$ are two identical or different basic amino acids;
$X^{12}$ are two identical or different hydrophobic amino acids;
$X^{13}$ are two identical or different basic amino acids;
$X^{14}$ are two identical or different hydrophobic amino acids;
$X^{15}$ is absent or a basic amino acid.

The above hydrophobic amino acid can be selected from any hydrophobic amino acids, and preferably from the group consisting of alanine, valine, leucine and isoleucine. The above basic amino acid can be selected from any basic amino acids, and preferably from the group consisting of lysine, arginine and histidine. More preferably, the above antimicrobial peptide can include peptides with amino acid sequences represented by the sequence identification number (SEQ ID NO) 1 to 34 in the list of sequences in Table 1 and the sequence listing.

Also, the present invention provides antimicrobial peptide analogs including peptides whose sequence is represented by the following sequence equation (II) wherein the residues at N-terminus and C-terminus are exchanged centering around the central fragment ($X^4 X^5 X^6 X^7 X^8$) of the above sequence equation (I);

$$[\text{N-terminus-}X^{15}X^{14}X^{13}X^{12}X^{11}X^{10}X^9X^4X^5X^6X^7X^8X^3X^2X^1\text{-C-terminus}] \quad (II)$$

$$\underbrace{\phantom{XXXXXXXX}}_{\text{central fragment}}$$

wherein,
$X^1$ is absent or a basic amino acid;
$X^2$ are two identical or different hydrophobic amino acids;
$X^3$ is a basic amino acid;
$X^4$ is glutamine or asparagine;
$X^5$ is phenylalanine or tryptophane;
$X^6$ is proline;
$X^7$ is isoleucine or valine;
$X^8$ is glycine;
$X^9$ is a basic amino acid;
$X^{10}$ are two identical or different hydrophobic amino acids;
$X^{11}$ are two identical or different basic amino acids;
$X^{12}$ are two identical or different hydrophobic amino acids;
$X^{13}$ are two identical or different basic amino acids;
$X^{14}$ are two identical or different hydrophobic amino acids;
$X^{15}$ is absent or a basic amino acid.

The above hydrophobic amino acid can be selected from any hydrophobic amino acids, and preferably from the group consisting of alanine, valine, leucine and isoleucine. The above basic amino acid can be selected from any basic amino acids, and preferably from the group consisting of lysine, arginine and histidine. More preferably, the above antimicrobial peptide can include peptides with amino acid sequences represented by SEQ ID NO: 35 to 68 in the list of sequences in Table 1 and the sequence listing.

Also, the present invention provides antimicrobial peptide analogs including the peptides represented by the above sequence equation (I) and (II), which are amidated at C-terminus. Preferably, the above antimicrobial peptide can include peptides with amino acid sequences represented by SEQ ID NO: 69 to 72 in the list of sequences in Table 1 and the sequence listing. As can be seen in Table 2, the antimicrobial peptides whose C-terminus is amidated show improved antimicrobial activities against Gram-positive and Gram-negative bacteria, and fungi.

Also the present invention provides antimicrobial compositions comprising one or more antimicrobial peptides according to the present invention as effective ingredients in a pharmacologically effective amount. The above antimicrobial composition can comprise pharmacologically acceptable carriers or other known antimicrobial materials in addition to the antimicrobial peptides according to the present invention.

The peptides according to the present invention can be synthesized by using the methods known to person skilled in the field, for example by using automatic peptide synthesizer. For instance, the above peptide according to the present invention can be obtained by genetic modification technique by synthesizing the gene encoding the fusion protein including the peptide of the present invention by genetic modification, by transforming the host microorganisms with the synthesized gene, and by obtaining the peptide from the fusion protein separated from the host microorganism.

The preparation method of the antimicrobial peptide according to the preferable specific embodiment of the present invention includes the steps of
- synthesizing a peptide by using automatic peptide synthesizer;
- measuring antimicrobial activity, cell penetration activity and hemolytic activity of the above synthesized peptide;
- synthesizing the peptide analogs wherein the amino acid residues of the above synthesized peptide is substituted, added or deleted; and
- selecting the peptide analog with strong antimicrobial activity and high safety by repeating the above steps.

The microorganisms used in the present invention include Gram-positive bacteria such as *Bacillus subtilis* (ATCC 62037), *Staphylococcus aureus* (ATCC 15752) and *Streptococcus mutans* (ATCC 25175), Gram-negative bacteria such as *Escherichia coli* (ATCC 27325), *Salmonella enteritidis* (ATCC 15277) and *Pseudomonas putida* (ATCC 17426) and fungi such as *Candida albicans* (ATCC 10231), *Saccharomyces cerevisiae* (ATCC 44774) and *Cryptococcus neoformans* (ATCC 34881), obtained from American Type Culture Collection (ATCC).

EXAMPLES

Figure 1A:
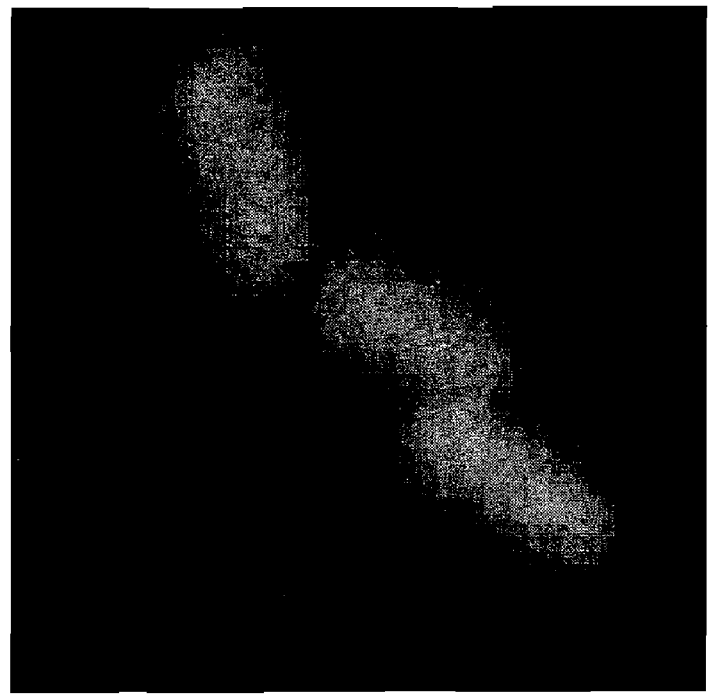
FIGS. 1A~1D are the results of analyzing the cell penetration activity of the new antimicrobial peptides by confocal microscopy. To emphasize the location of the antimicrobial peptides, color was eliminated from the images. The white area in FIGS. 1A~1D is the antimicrobial peptide penetrated within the cell.

This invention is explained in more detail based on the following Examples but they should not be construed as limiting the scope of this invention.

Example 1

Preparation of New Antimicrobial Peptide Analogs

The peptides with the amino acid sequences listed in the below Table 1 were synthesized by using automatic peptide synthesizer (Milligen 9050, Millipore, USA) and were separated and purified by using C18 reverse phase High Performance Liquid Chromatography (HPLC, Waters Associates, USA).

TABLE 1

Amino acid sequence of peptide analogs

| Peptide | Amino Acid Sequence |
|---|---|
| SEQ ID NO 1 | RVVRQWPIGRVVRRVVRRVVR |
| SEQ ID NO 2 | KVVKQWPIGKVVKKVVKKVVK |
| SEQ ID NO 3 | RLLRQWPIGRLLRRLLRRLLR |
| SEQ ID NO 4 | KLLKQWPIGKLLKKLLKKLLK |
| SEQ ID NO 5 | RVLRQWPIGRVLRRVLRRVLR |
| SEQ ID NO 6 | KVLKQWPIGKVLKKVLKKVLK |
| SEQ ID NO 7 | RLVRQWPIGRLVRRLVRRLVR |
| SEQ ID NO 8 | KLVKQWPIGKLVKKLVKKLVK |
| SEQ ID NO 9 | RVVKQWPIGRVVKRVVKRVVK |

TABLE 1-continued

Amino acid sequence of peptide analogs

| Peptide | Amino Acid Sequence |
|---|---|
| SEQ ID NO 10 | KVVRQWPIGKVVRKVVRKVVR |
| SEQ ID NO 11 | RLLKQWPIGRLLKRLLKRLLK |
| SEQ ID NO 12 | KLLRQWPIGKLLRKLLRKLLR |
| SEQ ID NO 13 | RVLKQWPIGRVLKRVLKRVLK |
| SEQ ID NO 14 | KVLRQWPIGKVLRKVLRKVLR |
| SEQ ID NO 15 | RLVKQWPIGRLVKRLVKRLVK |
| SEQ ID NO 16 | KLVRQWPIGKLVRKLVRKLVR |
| SEQ ID NO 17 | KLVRQFPVGKLVRKLVRKLVR |
| SEQ ID NO 18 | RVVRNWPIGRVVRRVVRRVVR |
| SEQ ID NO 19 | KVVKNWPIGKVVKKVVKKVVK |
| SEQ ID NO 20 | RLLRNWPIGRLLRRLLRRLLR |
| SEQ ID NO 21 | KLLKNWPIGKLLKKLLKKLLK |
| SEQ ID NO 22 | RVLRNWPIGRVLRRVLRRVLR |
| SEQ ID NO 23 | KVLKNWPIGKVLKKVLKKVLK |
| SEQ ID NO 24 | RLVRNWPIGRLVRRLVRRLVR |
| SEQ ID NO 25 | KLVKNWPIGKLVKKLVKKLVK |
| SEQ ID NO 26 | RVVKNWPIGRVVKRVVKRVVK |
| SEQ ID NO 27 | KVVRNWPIGKVVRKVVRKVVR |
| SEQ ID NO 28 | RLLKNWPIGRLLKRLLKRLLK |
| SEQ ID NO 29 | KLLRNWPIGKLLRKLLRKLLR |
| SEQ ID NO 30 | RVLKNWPIGRVLKRVLKRVLK |
| SEQ ID NO 31 | KVLRNWPIGKVLRKVLRKVLR |
| SEQ ID NO 32 | RLVKNWPIGRLVKRLVKRLVK |
| SEQ ID NO 33 | KLVRNWPIGKLVRKLVRKLVR |
| SEQ ID NO 34 | KLVRNFPVGKLVRKLVRKLVR |
| SEQ ID NO 35 | RVVRRVVRRVVRQWPIGRVVR |
| SEQ ID NO 36 | KVVKKVVKKVVKQWPIGKVVK |
| SEQ ID NO 37 | RLLRRLLRRLLRQWPIGRLLR |
| SEQ ID NO 38 | KLLKKLLKKLLKQWPIGKLLK |
| SEQ ID NO 39 | RVLRRVLRRVLRQWPIGRVLR |
| SEQ ID NO 40 | KVLKKVLKKVLKQWPIGKVLK |
| SEQ ID NO 41 | RLVRRLVRRLVRQWPIGRLVR |
| SEQ ID NO 42 | KLVKKLVKKLVKQWPIGKLVK |
| SEQ ID NO 43 | RVVKRVVKRVVKQWPIGRVVK |
| SEQ ID NO 44 | KVVRKVVRKVVRQWPIGKVVR |
| SEQ ID NO 45 | RLLKRLLKRLLKQWPIGRLLK |
| SEQ ID NO 46 | KLLRKLLRKLLRQWPIGKLLR |
| SEQ ID NO 47 | RVLKRVLKRVLKQWPIGRVLK |
| SEQ ID NO 48 | KVLRKVLRKVLRQWPIGKVLR |
| SEQ ID NO 49 | RLVKRLVKRLVKQWPIGRLVK |
| SEQ ID NO 50 | KLVRKLVRKLVRQWPIGKLVR |
| SEQ ID NO 51 | KLVRKLVRKLVRQFPVGKLVR |
| SEQ ID NO 52 | RVVRRVVRRVVRNWPIGRVVR |
| SEQ ID NO 53 | KVVKKVVKKVVKNWPIGKVVK |
| SEQ ID NO 54 | RLLRRLLRRLLRNWPIGRLLR |
| SEQ ID NO 55 | KLLKKLLKKLLKNWPIGKLLK |
| SEQ ID NO 56 | RVLRRVLRRVLRNWPIGRVLR |
| SEQ ID NO 57 | KVLKKVLKKVLKNWPIGKVLK |
| SEQ ID NO 58 | RLVRRLVRRLVRNWPIGRLVR |
| SEQ ID NO 59 | KLVKKLVKKLVKNWPIGKLVK |
| SEQ ID NO 60 | RVVKRVVKRVVKNWPIGRVVK |
| SEQ ID NO 61 | KVVRKVVRKVVRNWPIGKVVR |
| SEQ ID NO 62 | RLLKRLLKRLLKNWPIGRLLK |
| SEQ ID NO 63 | KLLRKLLRKLLRNWPIGKLLR |
| SEQ ID NO 64 | RVLKRVLKRVLKNWPIGRVLK |
| SEQ ID NO 65 | KVLRKVLRKVLRNWPIGKVLR |
| SEQ ID NO 66 | RLVKRLVKRLVKNWPIGRLVK |
| SEQ ID NO 67 | KLVRKLVRKLVRNWPIGKLVR |
| SEQ ID NO 68 | KLVRKLVRKLVRNFPVGKLVR |
| SEQ ID NO 69 | KLVRQWPIGKLVRKLVRKLVR-amide |
| SEQ ID NO 70 | RLVKNWPIGRLVKRLVKRLVK-amide |
| SEQ ID NO 71 | KLVRKVLRKVLRQWPIGKVLR-amide |
| SEQ ID NO 72 | RVLKRVLKRVLKNWPIGRVLK-amide |

Example 2

Determination of Antimicrobial Activity of Peptides and their Analogs

The antimicrobial activity of the peptides prepared in Example 1 was determined against microorganisms by 96-well microdilution minimal inhibitory concentration assay. After overnight culturing the bacteria and fungi in trypticase soy broth (TSB) and Saboraud (SAB) at 37° C. and 30° C., respectively, they were inoculated in new media and cultured for 2 hours to exponential growth phase. After diluting the microorganisms to $10^5$ per 1 ml, 190 µl was inoculated in each 96-well plate, and 10 µl of serially diluted peptides were added in each well. The 96-well plate was cultured for 12 hours, and the absorbance was determined in well to determine the minimum concentration where the microorganisms cannot grow as the minimum inhibitory concentration (MIC). The result is shown in Table 2.

As can be seen in Table 2, MIC of the peptides prepared in Example 1 was 1-2 µl, whereas MIC of magainin was 32-128 µl against Gram-positive bacteria, Gram-negative bacteria and fungi. The results indicate that the peptides prepared in Example 1 have 32-128 times stronger antimicrobial activity than magainin.

TABLE 2

Minimum Inhibitory Concentration of Peptide analogs

| Microorganism | Minimum Inhibitory Concentration (µg/ml) SEQ ID NO | | | | | | | | | | |
|---|---|---|---|---|---|---|---|---|---|---|---|
| | 1 | 2 | 3 | 4 | 5 | 8 | 10 | 11 | 13 | 16 | 17 |
| Gram-positive bacteria | | | | | | | | | | | |
| *Bacillus subtilis* | 2 | 1 | 2 | 2 | 1 | 1 | 1 | 1 | 2 | 2 | 2 |
| *Staphylococcus aureus* | 1 | 1 | 1 | 1 | 1 | 1 | 1 | 1 | 1 | 1 | 1 |
| *Streptococcus mutans* | 2 | 2 | 1 | 1 | 1 | 2 | 2 | 2 | 2 | 2 | 2 |
| Gram-negative bacteria | | | | | | | | | | | |
| *Escherichia coli* | 1 | 1 | 2 | 1 | 1 | 1 | 1 | 1 | 1 | 1 | 1 |
| *Salmonella enteritidis* | 1 | 1 | 1 | 1 | 1 | 1 | 1 | 2 | 1 | 1 | 1 |
| *Pseudomonas putida* | 1 | 1 | 1 | 1 | 1 | 1 | 1 | 1 | 1 | 1 | 1 |
| Fungi | | | | | | | | | | | |
| *Candida albicans* | 2 | 1 | 1 | 1 | 1 | 2 | 2 | 1 | 1 | 1 | 1 |
| *Cryptococcus neoformans* | 1 | 1 | 1 | 1 | 1 | 1 | 1 | 1 | 1 | 1 | 1 |
| *Saccharomyces cerevisiae* | 2 | 2 | 2 | 2 | 2 | 2 | 2 | 2 | 2 | 1 | 1 |

| Microorganism | Minimum Inhibitory Concentration (µg/ml) SEQ ID NO | | | | | | | | | | |
|---|---|---|---|---|---|---|---|---|---|---|---|
| | 18 | 19 | 20 | 21 | 23 | 24 | 26 | 29 | 31 | 32 | 34 |
| Gram-positive bacteria | | | | | | | | | | | |
| *Bacillus subtilis* | 1 | 2 | 2 | 1 | 1 | 1 | 1 | 1 | 1 | 1 | 1 |
| *Staphylococcus aureus* | 1 | 1 | 1 | 1 | 1 | 1 | 1 | 1 | 1 | 1 | 1 |
| *Streptococcus mutans* | 2 | 1 | 2 | 2 | 2 | 1 | 1 | 2 | 2 | 2 | 2 |
| Gram-negative bacteria | | | | | | | | | | | |
| *Escherichia coil* | 1 | 2 | 1 | 1 | 1 | 1 | 2 | 1 | 1 | 1 | 1 |
| *Salmonella enteritidis* | 2 | 1 | 2 | 2 | 2 | 2 | 1 | 1 | 1 | 1 | 1 |
| *Pseudomonas putida* | 1 | 1 | 1 | 1 | 1 | 1 | 1 | 1 | 1 | 1 | 1 |
| Fungi | | | | | | | | | | | |
| *Candida albicans* | 1 | 1 | 1 | 2 | 1 | 2 | 2 | 1 | 1 | 1 | 1 |
| *Cryptococcus neoformans* | 1 | 1 | 1 | 1 | 1 | 1 | 1 | 1 | 1 | 1 | 1 |
| *Saccharomyces cerevisiae* | 1 | 2 | 2 | 1 | 1 | 2 | 2 | 2 | 2 | 2 | 1 |

| Microorganism | Minimum Inhibitory Concentration (µg/ml) SEQ ID NO | | | | | | | | | | |
|---|---|---|---|---|---|---|---|---|---|---|---|
| | 35 | 36 | 37 | 38 | 39 | 42 | 44 | 45 | 47 | 50 | 51 |
| Gram-positive bacteria | | | | | | | | | | | |
| *Bacillus subtilis* | 1 | 1 | 1 | 1 | 2 | 1 | 2 | 1 | 1 | 1 | 1 |
| *Staphylococcus aureus* | 1 | 1 | 1 | 1 | 2 | 1 | 1 | 1 | 1 | 1 | 1 |
| *Streptococcus mutans* | 1 | 2 | 1 | 2 | 2 | 2 | 2 | 1 | 2 | 1 | 1 |
| Gram-negative bacteria | | | | | | | | | | | |
| *Escherichia coli* | 2 | 2 | 1 | 2 | 1 | 1 | 1 | 1 | 1 | 1 | 1 |
| *Salmonella enteritidis* | 1 | 1 | 2 | 1 | 1 | 1 | 1 | 2 | 1 | 2 | 2 |
| *Pseudomonas putida* | 1 | 1 | 1 | 1 | 1 | 1 | 1 | 1 | 1 | 1 | 1 |
| Fungi | | | | | | | | | | | |
| *Candida albicans* | 1 | 2 | 2 | 2 | 2 | 1 | 2 | 2 | 1 | 1 | 1 |
| *Cryptococcus neoformans* | 1 | 1 | 2 | 1 | 1 | 1 | 1 | 2 | 1 | 1 | 1 |
| *Saccharomyces cerevisiae* | 2 | 2 | 2 | 2 | 2 | 1 | 1 | 2 | 2 | 2 | 2 |

TABLE 2-continued

Minimum Inhibitory Concentration of Peptide analogs

| Microorganism | Minimum Inhibitory Concentration (μg/ml) SEQ ID NO | | | | | | | | | | |
|---|---|---|---|---|---|---|---|---|---|---|---|
| | 52 | 53 | 54 | 55 | 57 | 58 | 60 | 63 | 65 | 66 | 68 |
| Gram-positive bacteria | | | | | | | | | | | |
| Bacillus subtilis | 1 | 1 | 1 | 1 | 1 | 1 | 1 | 1 | 2 | 1 | 1 |
| Staphylococcus aureus | 1 | 1 | 1 | 1 | 1 | 1 | 2 | 1 | 1 | 1 | 1 |
| Streptococcus mutans | 2 | 1 | 2 | 2 | 2 | 1 | 2 | 2 | 2 | 2 | 2 |
| Gram-negative bacteria | | | | | | | | | | | |
| Escherichia coli | 1 | 1 | 2 | 2 | 2 | 1 | 2 | 1 | 1 | 2 | 1 |
| Salmonella enteritidis | 2 | 1 | 1 | 1 | 1 | 1 | 2 | 2 | 2 | 1 | 1 |
| Pseudomonas putida | 1 | 1 | 1 | 1 | 1 | 1 | 1 | 1 | 1 | 1 | 1 |
| Fungi | | | | | | | | | | | |
| Candida albicans | 1 | 2 | 1 | 1 | 1 | 2 | 1 | 1 | 1 | 1 | 1 |
| Cryptococcus neoformans | 1 | 1 | 1 | 1 | 1 | 1 | 1 | 1 | 1 | 1 | 1 |
| Saccharomyces cerevisiae | 1 | 1 | 2 | 2 | 2 | 2 | 1 | 2 | 1 | 2 | 2 |

| Microorganism | Minimum Inhibitory Concentration (μg/ml) SEQ ID NO | | | | |
|---|---|---|---|---|---|
| | 69 | 70 | 71 | 72 | Magainin |
| Gram-positive bacteria | | | | | |
| Bacillus subtilis | 1 | 1 | 1 | 1 | 64 |
| Staphylococcus aureus | 1 | 1 | 1 | 1 | 64 |
| Streptococcus mutans | 1 | 2 | 1 | 2 | 128 |
| Gram-negative bacteria | | | | | |
| Escherichia coli | 1 | 1 | 1 | 1 | 128 |
| Salmonella enteritidis | 2 | 1 | 1 | 1 | 32 |
| Pseudomonas putida | 1 | 1 | 1 | 1 | 64 |
| Fungi | | | | | |
| Candida albicans | 1 | 1 | 1 | 1 | 32 |
| Cryptococcus neoformans | 1 | 1 | 1 | 1 | 32 |
| Saccharomyces cerevisiae | 2 | 1 | 2 | 2 | 32 |

Example 3

Determination of Cell Penetration Activity of Peptides and their Analogs

The cell penetration activity of the peptides prepared in Example 1 was observed by confocal microscopy. After inoculating and culturing E. coli in trypticase soy broth at 37° C. overnight, they were inoculated in new media and cultured for 2 hours to exponential growth phase. After washing E. coli with 10 mM NAPB (sodium phosphate buffer) and diluting to $10^5$ CFU/ml, the above diluted E. coli was fixed for 30 min on glass-slides coated with poly-L-lysine. The N-terminus of the peptides prepared in Example 1 was labeled with FITC (fluoresceinisothicyanate), and the labeled peptides were applied to E. coli fixed on the glass-slides for 5 minutes. The glass-slides were washed with 10 mM NAPB and observed them by confocal microscopy. The obtained results are shown in FIGS. 1a~1d.

Figure 1B:
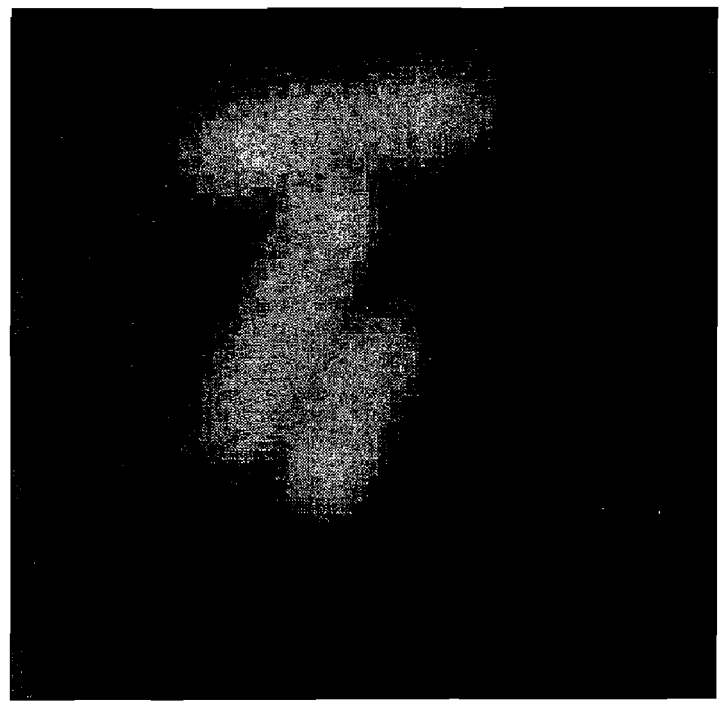
Figure 1C:
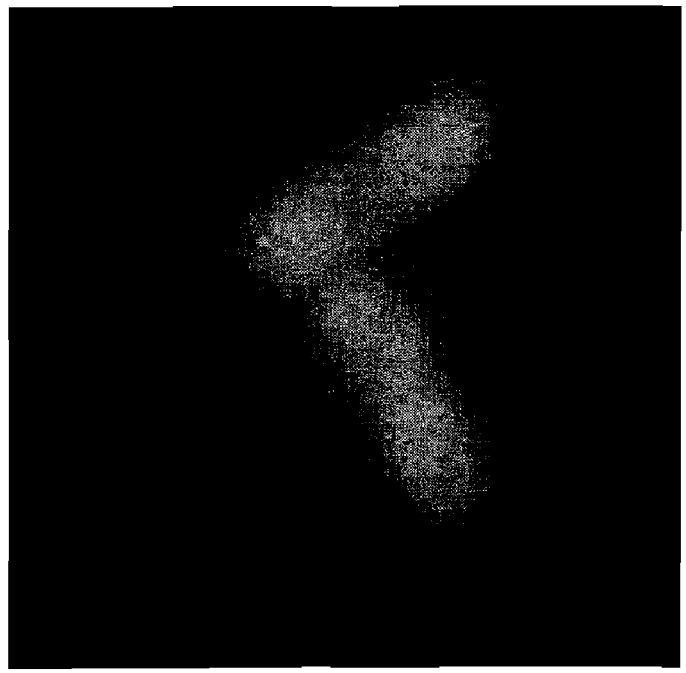
Figure 1D:
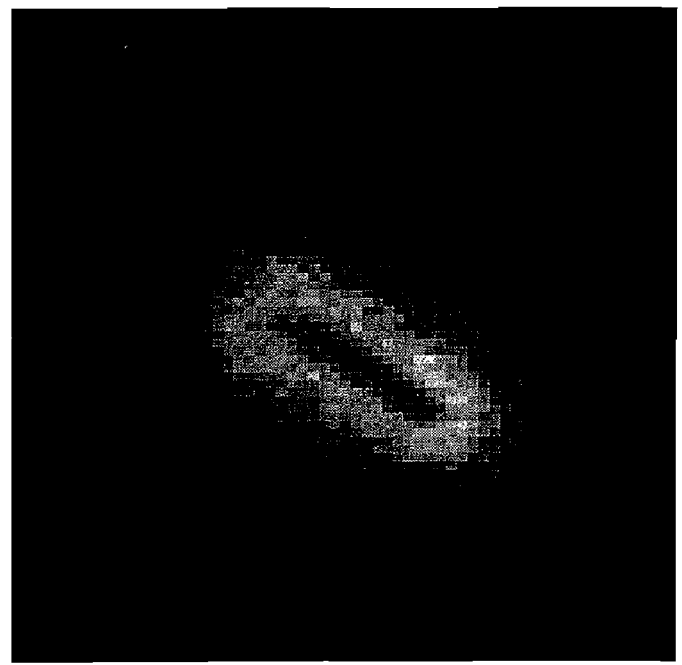

FIGS. 1A, 1B and 1C are photographs obtained by confocal microscopy showing that peptides of SEQ ID NO: 1, 33 and 65 penetrate into E. coli cells. FIG. 1D is a photograph obtained by confocal microscopy of E. coli treated with magainin, which can bind with cell membrane to kill the microorganisms.

Example 4

Measurement of Hemolytic Activity of Peptides and their Analogs

After separating the precipitated human red blood cells (hRBC) from 3 ml of human blood, they were washed with PBS (phosphate buffered saline) and diluted to make the total volume of 20 ml. In 190 μl of the prepared hRBC solution, 10 μl of each peptide sample (4 μg/μl) prepared in Example 1 was added to make the final concentration of 200 μg/ml, reacted for 1 h at 37° C. and centrifuged for 5 min at 4000 rpm. After diluting 100 μl of the supernatant of each sample by 10 times in PBS buffer solution, absorbance was measured at 576 nm ($A_{576}$). The absorbance of the sample treated with 0.2% Triton X-100 was set to represent 100% hemolysis and the percent (%) hemolysis of each sample was relatively calculated from each measured absorbance, as shown in Table 3.

As can be seen in Table 3, all of the peptides prepared in Example 1 showed less than 1% of hemolysis activities. Such result implies that the peptides prepared in Example 1 are not toxic to human cells. In contrast, melittin, which was included in this Example for comparison, is a hemolytic peptide and did destroy almost all hRBC at the concentration of 200 μg/ml.

TABLE 3

Hemolytic activity of peptide analogs

| SEQ ID NO | A567 | % hemolysis | SEQ ID NO | A567 | % hemolysis |
|---|---|---|---|---|---|
| 1 | 0.013 | 0.4 | 2 | 0.017 | 0.5 |
| 3 | 0.022 | 0.6 | 4 | 0.025 | 0.8 |
| 5 | 0.019 | 0.6 | 8 | 0.021 | 0.7 |
| 10 | 0.016 | 0.5 | 11 | 0.013 | 0.4 |
| 13 | 0.011 | 0.3 | 16 | 0.014 | 0.4 |
| 17 | 0.012 | 0.4 | 18 | 0.014 | 0.4 |
| 19 | 0.015 | 0.5 | 20 | 0.018 | 0.6 |
| 21 | 0.012 | 0.4 | 23 | 0.013 | 0.4 |
| 24 | 0.016 | 0.5 | 26 | 0.011 | 0.3 |
| 29 | 0.015 | 0.5 | 31 | 0.012 | 0.4 |
| 32 | 0.013 | 0.4 | 34 | 0.011 | 0.3 |
| 35 | 0.017 | 0.5 | 36 | 0.018 | 0.6 |
| 37 | 0.016 | 0.5 | 38 | 0.019 | 0.6 |
| 39 | 0.022 | 0.6 | 42 | 0.014 | 0.4 |
| 44 | 0.021 | 0.7 | 45 | 0.015 | 0.5 |
| 47 | 0.017 | 0.5 | 50 | 0.013 | 0.4 |
| 51 | 0.016 | 0.5 | 52 | 0.016 | 0.5 |
| 53 | 0.015 | 0.5 | 54 | 0.010 | 0.3 |
| 55 | 0.020 | 0.6 | 57 | 0.025 | 0.8 |
| 58 | 0.013 | 0.4 | 60 | 0.016 | 0.5 |
| 63 | 0.012 | 0.4 | 65 | 0.023 | 0.7 |
| 66 | 0.015 | 0.5 | 68 | 0.015 | 0.5 |
| 69 | 0.018 | 0.6 | 70 | 0.017 | 0.5 |
| 71 | 0.013 | 0.4 | 72 | 0.015 | 0.5 |
| 0.2% Triton X-100 | 3.21 | 100 | Melittin | 3.17 | 99 |

TABLE 4

The percent (%) identity between SEQ ID No. 1 and SEQ ID NOS. 2 to 34. The percent identity was calculated by dividing the number of amino acid positions in SEQ ID NOS. 2 to 34 that are identical to the same amino acid position in SEQ ID No. 1 by the total number of amino acids in SEQ ID No. 1, then multiplying by 100.

| | The number of amino acids identical with Seq. No 1 | Identity (%) |
|---|---|---|
| Seq. No 1 | 21 | 100 |
| Seq. No 2 | 13 | 61.9 |
| Seq. No 3 | 13 | 61.9 |
| Seq. No 4 | 5 | 23.8 |
| Seq. No 5 | 17 | 61.9 |
| Seq. No 6 | 9 | 42.9 |
| Seq. No 7 | 17 | 81.0 |
| Seq. No 8 | 9 | 42.9 |
| Seq. No 9 | 17 | 81.0 |
| Seq. No 10 | 17 | 81.0 |
| Seq. No 11 | 9 | 42.9 |
| Seq. No 12 | 9 | 42.9 |
| Seq. No 13 | 13 | 61.9 |
| Seq. No 14 | 13 | 61.9 |
| Seq. No 15 | 13 | 61.9 |
| Seq. No 16 | 13 | 61.9 |
| Seq. No 17 | 11 | 52.4 |
| Seq. No 18 | 20 | 95.2 |
| Seq. No 19 | 12 | 57.1 |
| Seq. No 20 | 12 | 57.1 |
| Seq. No 21 | 4 | 19.0 |
| Seq. No 22 | 16 | 76.2 |
| Seq. No 23 | 8 | 38.1 |
| Seq. No 24 | 16 | 76.2 |
| Seq. No 25 | 8 | 38.1 |
| Seq. No 26 | 16 | 76.2 |
| Seq. No 27 | 16 | 76.2 |
| Seq. No 28 | 8 | 38.1 |
| Seq. No 29 | 8 | 38.1 |
| Seq. No 30 | 12 | 57.1 |
| Seq. No 31 | 12 | 57.1 |
| Seq. No 32 | 12 | 57.1 |
| Seq. No 33 | 12 | 57.1 |
| Seq. No 34 | 10 | 47.6 |

INDUSTRIAL APPLICABILITY

As written above, the antimicrobial peptides and their analogs synthesized in the present invention show strong antimicrobial activity against Gram-positive bacteria, Gram-negative bacteria and fungi. Since the peptides of the present invention strongly inhibits the growth of microorganisms without hemolytic activity, the peptides of the present invention can be used as excellent antimicrobial agents such as wound healing enhancer, external wound treatment agent, mouth wash, eye-drops, etc. Therefore the present invention will become valuable in the biomedical industry.

The invention claimed is:

1. An antimicrobial peptide including the amino acid sequence represented as the following sequence equation (I):

N-terminus—$X^1X^2X^3X^4X^5X^6X^7X^8X^9X^{10}X^{11}X^{12}X^{13}X^{14}X^{15}$—C-terminus (I)

wherein,
- $X^1$ is absent or a basic amino acid;
- $X^2$ are two identical or different hydrophobic amino acids;
- $X^3$ is a basic amino acid;
- $X^4$ is glutamine or asparagines;
- $X^5$ is phenylalanine or tryptophan;
- $X^6$ is proline;
- $X^7$ is isoleucine or valine;
- $X^8$ is glycine;
- $X^9$ is a basic amino acid;
- $X^{10}$ are two identical or different hydrophobic amino acids;
- $X^{11}$ are two identical or different basic amino acids;
- $X^{12}$ are two identical or different hydrophobic amino acids;
- $X^{13}$ are two identical or different basic amino acids;
- $X^{14}$ are two identical or different hydrophobic amino acids;
- $X^{15}$ is absent or a basic amino acid.

2. An antimicrobial composition comprising at least one antimicrobial peptide according to claim 1 as effective ingredient in a pharmacologically effective amount.

3. The antimicrobial peptide according to claim 1, wherein the C-terminus of the amino acid sequence is amidated.

4. An antimicrobial composition comprising at least one antimicrobial peptide according to claim 3 as effective ingredient in a pharmacologically effective amount.

5. The antimicrobial peptide according to claim 1, wherein one of the amino acid sequences is selected from SEQ ID NOS: 1 to 34.

6. An antimicrobial composition comprising at least one antimicrobial peptide according to claim 5 as effective ingredient in a pharmacologically effective amount.

7. The antimicrobial peptide according to claim 5, wherein the C-terminus of the amino acid sequence is amidated.

8. An antimicrobial composition comprising at least one antimicrobial peptide according to claim 7 as effective ingredient in a pharmacologically effective amount.

9. The antimicrobial peptide according to claim 1, wherein the amino acid sequence is SEQ ID NO: 1.

10. An antimicrobial composition comprising at least one or more antimicrobial peptide according to claim 9 as effective ingredient in a pharmacologically effective amount.

11. The antimicrobial peptide according to claim 9, wherein the C-terminus of the amino acid sequence is amidated.

12. An antimicrobial composition comprising at least one or more antimicrobial peptide according to claim 11 as effective ingredient in a pharmacologically effective amount.

* * * * *

SEQUENCE LISTING

<160> NUMBER OF SEQ ID NOS: 72

<210> SEQ ID NO 1
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 1

Arg Val Val Arg Gln Trp Pro Ile Gly Arg Val Val Arg Arg Val Val
1               5                   10                  15

Arg Arg Val Val Arg
            20

```
<210> SEQ ID NO 2
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 2

Lys Val Val Lys Gln Trp Pro Ile Gly Lys Val Val Lys Val Val
 1               5                  10                  15

Lys Lys Val Val Lys
            20

<210> SEQ ID NO 3
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 3

Arg Leu Leu Arg Gln Trp Pro Ile Gly Arg Leu Leu Arg Leu Leu
 1               5                  10                  15

Arg Arg Leu Leu Arg
            20

<210> SEQ ID NO 4
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 4

Lys Leu Leu Lys Gln Trp Pro Ile Gly Lys Leu Leu Lys Leu Leu
 1               5                  10                  15

Lys Lys Leu Leu Lys
            20

<210> SEQ ID NO 5
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 5

Arg Val Leu Arg Gln Trp Pro Ile Gly Arg Val Leu Arg Val Leu
 1               5                  10                  15

Arg Arg Val Leu Arg
            20

<210> SEQ ID NO 6
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 6

Lys Val Leu Lys Gln Trp Pro Ile Gly Lys Val Leu Lys Val Leu
 1               5                  10                  15

Lys Lys Val Leu Lys
```

-continued

```
                    20

<210> SEQ ID NO 7
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 7

Arg Leu Val Arg Gln Trp Pro Ile Gly Arg Leu Val Arg Arg Leu Val
 1               5                  10                  15

Arg Arg Leu Val Arg
            20

<210> SEQ ID NO 8
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 8

Lys Leu Val Lys Gln Trp Pro Ile Gly Lys Leu Val Lys Lys Leu Val
 1               5                  10                  15

Lys Lys Leu Val Lys
            20

<210> SEQ ID NO 9
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 9

Arg Val Val Lys Gln Trp Pro Ile Gly Arg Val Val Lys Arg Val Val
 1               5                  10                  15

Lys Arg Val Val Lys
            20

<210> SEQ ID NO 10
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 10

Lys Val Val Arg Gln Trp Pro Ile Gly Lys Val Val Arg Lys Val Val
 1               5                  10                  15

Arg Lys Val Val Arg
            20

<210> SEQ ID NO 11
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 11

Arg Leu Leu Lys Gln Trp Pro Ile Gly Arg Leu Leu Lys Arg Leu Leu
 1               5                  10                  15
```

```
Lys Arg Leu Leu Lys
            20

<210> SEQ ID NO 12
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 12

Lys Leu Leu Arg Gln Trp Pro Ile Gly Lys Leu Leu Arg Lys Leu Leu
  1               5                  10                  15

Arg Lys Leu Leu Arg
            20

<210> SEQ ID NO 13
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 13

Arg Val Leu Lys Gln Trp Pro Ile Gly Arg Val Leu Lys Arg Val Leu
  1               5                  10                  15

Lys Arg Val Leu Lys
            20

<210> SEQ ID NO 14
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 14

Lys Val Leu Arg Gln Trp Pro Ile Gly Lys Val Leu Arg Lys Val Leu
  1               5                  10                  15

Arg Lys Val Leu Arg
            20

<210> SEQ ID NO 15
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 15

Arg Leu Val Lys Gln Trp Pro Ile Gly Arg Leu Val Lys Arg Leu Val
  1               5                  10                  15

Lys Arg Leu Val Lys
            20

<210> SEQ ID NO 16
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 16

Lys Leu Val Arg Gln Trp Pro Ile Gly Lys Leu Val Arg Lys Leu Val
  1               5                  10                  15
```

```
Arg Lys Leu Val Arg
            20

<210> SEQ ID NO 17
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 17

Lys Leu Val Arg Gln Phe Pro Val Gly Lys Leu Val Arg Lys Leu Val
  1               5                  10                  15

Arg Lys Leu Val Arg
            20

<210> SEQ ID NO 18
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 18

Arg Val Val Arg Asn Trp Pro Ile Gly Arg Val Val Arg Arg Val Val
  1               5                  10                  15

Arg Arg Val Val Arg
            20

<210> SEQ ID NO 19
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 19

Lys Val Val Lys Asn Trp Pro Ile Gly Lys Val Val Lys Lys Val Val
  1               5                  10                  15

Lys Lys Val Val Lys
            20

<210> SEQ ID NO 20
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 20

Arg Leu Leu Arg Asn Trp Pro Ile Gly Arg Leu Leu Arg Arg Leu Leu
  1               5                  10                  15

Arg Arg Leu Leu Arg
            20

<210> SEQ ID NO 21
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 21

Lys Leu Leu Lys Asn Trp Pro Ile Gly Lys Leu Leu Lys Lys Leu Leu
```

```
                1               5                  10                 15
Lys Lys Leu Leu Lys
            20

<210> SEQ ID NO 22
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 22

Arg Val Leu Arg Asn Trp Pro Ile Gly Arg Val Leu Arg Val Leu
  1               5                  10                 15

Arg Arg Val Leu Arg
            20

<210> SEQ ID NO 23
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 23

Lys Val Leu Lys Asn Trp Pro Ile Gly Lys Val Leu Lys Val Leu
  1               5                  10                 15

Lys Lys Val Leu Lys
            20

<210> SEQ ID NO 24
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 24

Arg Leu Val Arg Asn Trp Pro Ile Gly Arg Leu Val Arg Leu Val
  1               5                  10                 15

Arg Arg Leu Val Arg
            20

<210> SEQ ID NO 25
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 25

Lys Leu Val Lys Asn Trp Pro Ile Gly Lys Leu Val Lys Leu Val
  1               5                  10                 15

Lys Lys Leu Val Lys
            20

<210> SEQ ID NO 26
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 26
```

-continued

Arg Val Val Lys Asn Trp Pro Ile Gly Arg Val Val Lys Val Val
 1               5                  10                 15

Lys Arg Val Val Lys
         20

<210> SEQ ID NO 27
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 27

Lys Val Val Arg Asn Trp Pro Ile Gly Lys Val Val Arg Lys Val Val
 1               5                  10                 15

Arg Lys Val Val Arg
         20

<210> SEQ ID NO 28
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 28

Arg Leu Leu Lys Asn Trp Pro Ile Gly Arg Leu Leu Lys Arg Leu Leu
 1               5                  10                 15

Lys Arg Leu Leu Lys
         20

<210> SEQ ID NO 29
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 29

Lys Leu Leu Arg Asn Trp Pro Ile Gly Lys Leu Leu Arg Lys Leu Leu
 1               5                  10                 15

Arg Lys Leu Leu Arg
         20

<210> SEQ ID NO 30
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 30

Arg Val Leu Lys Asn Trp Pro Ile Gly Arg Val Leu Lys Arg Val Leu
 1               5                  10                 15

Lys Arg Val Leu Lys
         20

<210> SEQ ID NO 31
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 31

```
Lys Val Leu Arg Asn Trp Pro Ile Gly Lys Val Leu Arg Lys Val Leu
 1               5                  10                  15

Arg Lys Val Leu Arg
            20

<210> SEQ ID NO 32
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 32

Arg Leu Val Lys Asn Trp Pro Ile Gly Arg Leu Val Lys Arg Leu Val
 1               5                  10                  15

Lys Arg Leu Val Lys
            20

<210> SEQ ID NO 33
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 33

Lys Leu Val Arg Asn Trp Pro Ile Gly Lys Leu Val Arg Lys Leu Val
 1               5                  10                  15

Arg Lys Leu Val Arg
            20

<210> SEQ ID NO 34
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 34

Lys Leu Val Arg Asn Phe Pro Val Gly Lys Leu Val Arg Lys Leu Val
 1               5                  10                  15

Arg Lys Leu Val Arg
            20

<210> SEQ ID NO 35
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 35

Arg Val Val Arg Val Val Arg Val Val Arg Gln Trp Pro Ile
 1               5                  10                  15

Gly Arg Val Val Arg
            20

<210> SEQ ID NO 36
<211> LENGTH: 21
<212> TYPE: PRT
<213> ORGANISM: Artificial Sequence
<220> FEATURE:
<223> OTHER INFORMATION: antimicrobial peptide
```

```
<400> SEQUENCE: 36

Lys Val Val Lys Lys Val Val Lys Lys Val Val Lys Gln Trp Pro Ile
 1               5                  10                  15

Gly Lys Val Val Lys
            20

<210> SEQ ID NO 37
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 37

Arg Leu Leu Arg Arg Leu Leu Arg Arg Leu Leu Arg Gln Trp Pro Ile
 1               5                  10                  15

Gly Arg Leu Leu Arg
            20

<210> SEQ ID NO 38
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 38

Lys Leu Leu Lys Lys Leu Leu Lys Lys Leu Leu Lys Gln Trp Pro Ile
 1               5                  10                  15

Gly Lys Leu Leu Lys
            20

<210> SEQ ID NO 39
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 39

Arg Val Leu Arg Arg Val Leu Arg Arg Val Leu Arg Gln Trp Pro Ile
 1               5                  10                  15

Gly Arg Val Leu Arg
            20

<210> SEQ ID NO 40
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 40

Lys Val Leu Lys Lys Val Leu Lys Lys Val Leu Lys Gln Trp Pro Ile
 1               5                  10                  15

Gly Lys Val Leu Lys
            20

<210> SEQ ID NO 41
<211> LENGTH: 21
<212> TYPE: PRT
<213> ORGANISM: Artificial Sequence
<220> FEATURE:
<223> OTHER INFORMATION: antimicrobial peptide
```

```
<400> SEQUENCE: 41

Arg Leu Val Arg Arg Leu Val Arg Arg Leu Val Arg Gln Trp Pro Ile
 1               5                  10                  15

Gly Arg Leu Val Arg
            20

<210> SEQ ID NO 42
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 42

Lys Leu Val Lys Lys Leu Val Lys Lys Leu Val Lys Gln Trp Pro Ile
 1               5                  10                  15

Gly Lys Leu Val Lys
            20

<210> SEQ ID NO 43
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 43

Arg Val Val Lys Arg Val Val Lys Arg Val Val Lys Gln Trp Pro Ile
 1               5                  10                  15

Gly Arg Val Val Lys
            20

<210> SEQ ID NO 44
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 44

Lys Val Val Arg Lys Val Val Arg Lys Val Val Arg Gln Trp Pro Ile
 1               5                  10                  15

Gly Lys Val Val Arg
            20

<210> SEQ ID NO 45
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 45

Arg Leu Leu Lys Arg Leu Leu Lys Arg Leu Leu Lys Gln Trp Pro Ile
 1               5                  10                  15

Gly Arg Leu Leu Lys
            20

<210> SEQ ID NO 46
<211> LENGTH: 21
<212> TYPE: PRT
<213> ORGANISM: Artificial Sequence
<220> FEATURE:
```

<223> OTHER INFORMATION: antimicrobial peptide

<400> SEQUENCE: 46

Lys Leu Leu Arg Lys Leu Leu Arg Lys Leu Leu Arg Gln Trp Pro Ile
 1               5                  10                  15

Gly Lys Leu Leu Arg
            20

<210> SEQ ID NO 47
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 47

Arg Val Leu Lys Arg Val Leu Lys Arg Val Leu Lys Gln Trp Pro Ile
 1               5                  10                  15

Gly Arg Val Leu Lys
            20

<210> SEQ ID NO 48
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 48

Lys Val Leu Arg Lys Val Leu Arg Lys Val Leu Arg Gln Trp Pro Ile
 1               5                  10                  15

Gly Lys Val Leu Arg
            20

<210> SEQ ID NO 49
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 49

Arg Leu Val Lys Arg Leu Val Lys Arg Leu Val Lys Gln Trp Pro Ile
 1               5                  10                  15

Gly Arg Leu Val Lys
            20

<210> SEQ ID NO 50
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 50

Lys Leu Val Arg Lys Leu Val Arg Lys Leu Val Arg Gln Trp Pro Ile
 1               5                  10                  15

Gly Lys Leu Val Arg
            20

<210> SEQ ID NO 51
<211> LENGTH: 21
<212> TYPE: PRT
<213> ORGANISM: Artificial Sequence

```
<220> FEATURE:
<223> OTHER INFORMATION: antimicrobial peptide

<400> SEQUENCE: 51

Lys Leu Val Arg Lys Leu Val Arg Lys Leu Val Arg Gln Phe Pro Val
 1               5                  10                  15

Gly Lys Leu Val Arg
            20

<210> SEQ ID NO 52
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 52

Arg Val Val Arg Arg Val Val Arg Arg Val Val Arg Asn Trp Pro Ile
 1               5                  10                  15

Gly Arg Val Val Arg
            20

<210> SEQ ID NO 53
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 53

Lys Val Val Lys Lys Val Val Lys Lys Val Val Lys Asn Trp Pro Ile
 1               5                  10                  15

Gly Lys Val Val Lys
            20

<210> SEQ ID NO 54
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 54

Arg Leu Leu Arg Arg Leu Leu Arg Arg Leu Leu Arg Asn Trp Pro Ile
 1               5                  10                  15

Gly Arg Leu Leu Arg
            20

<210> SEQ ID NO 55
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 55

Lys Leu Leu Lys Lys Leu Leu Lys Lys Leu Leu Lys Asn Trp Pro Ile
 1               5                  10                  15

Gly Lys Leu Leu Lys
            20

<210> SEQ ID NO 56
<211> LENGTH: 21
<212> TYPE: PRT
```

<213> ORGANISM: Artificial Sequence
<220> FEATURE:
<223> OTHER INFORMATION: antimicrobial peptide

<400> SEQUENCE: 56

Arg Val Leu Arg Arg Val Leu Arg Arg Val Leu Arg Asn Trp Pro Ile
 1               5                  10                  15

Gly Arg Val Leu Arg
            20

<210> SEQ ID NO 57
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 57

Lys Val Leu Lys Lys Val Leu Lys Lys Val Leu Lys Asn Trp Pro Ile
 1               5                  10                  15

Gly Lys Val Leu Lys
            20

<210> SEQ ID NO 58
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 58

Arg Leu Val Arg Arg Leu Val Arg Arg Leu Val Arg Asn Trp Pro Ile
 1               5                  10                  15

Gly Arg Leu Val Arg
            20

<210> SEQ ID NO 59
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 59

Lys Leu Val Lys Lys Leu Val Lys Lys Leu Val Lys Asn Trp Pro Ile
 1               5                  10                  15

Gly Lys Leu Val Lys
            20

<210> SEQ ID NO 60
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 60

Arg Val Val Lys Arg Val Val Lys Arg Val Val Lys Asn Trp Pro Ile
 1               5                  10                  15

Gly Arg Val Val Lys
            20

<210> SEQ ID NO 61
<211> LENGTH: 21

```
<212> TYPE: PRT
<213> ORGANISM: Artificial Sequence
<220> FEATURE:
<223> OTHER INFORMATION: antimicrobial peptide

<400> SEQUENCE: 61

Lys Val Val Arg Lys Val Val Arg Lys Val Val Arg Asn Trp Pro Ile
 1               5                  10                  15

Gly Lys Val Val Arg
            20

<210> SEQ ID NO 62
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 62

Arg Leu Leu Lys Arg Leu Leu Lys Arg Leu Leu Lys Asn Trp Pro Ile
 1               5                  10                  15

Gly Arg Leu Leu Lys
            20

<210> SEQ ID NO 63
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 63

Lys Leu Leu Arg Lys Leu Leu Arg Lys Leu Leu Arg Asn Trp Pro Ile
 1               5                  10                  15

Gly Lys Leu Leu Arg
            20

<210> SEQ ID NO 64
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 64

Arg Val Leu Lys Arg Val Leu Lys Arg Val Leu Lys Asn Trp Pro Ile
 1               5                  10                  15

Gly Arg Val Leu Lys
            20

<210> SEQ ID NO 65
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 65

Lys Val Leu Arg Lys Val Leu Arg Lys Val Leu Arg Asn Trp Pro Ile
 1               5                  10                  15

Gly Lys Val Leu Arg
            20

<210> SEQ ID NO 66
```

```
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 66

Arg Leu Val Lys Arg Leu Val Lys Arg Leu Val Lys Asn Trp Pro Ile
 1               5                  10                  15

Gly Arg Leu Val Lys
            20

<210> SEQ ID NO 67
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 67

Lys Leu Val Arg Lys Leu Val Arg Lys Leu Val Arg Asn Trp Pro Ile
 1               5                  10                  15

Gly Lys Leu Val Arg
            20

<210> SEQ ID NO 68
<211> LENGTH: 21
<212> TYPE: PRT
<213> ORGANISM: Artificial Sequence
<220> FEATURE:
<223> OTHER INFORMATION: antimicrobial peptide

<400> SEQUENCE: 68

Lys Leu Val Arg Lys Leu Val Arg Lys Leu Val Arg Asn Phe Pro Val
 1               5                  10                  15

Gly Lys Leu Val Arg
            20

<210> SEQ ID NO 69
<211> LENGTH: 21
<212> TYPE: PRT
<213> ORGANISM: Artificial Sequence
<220> FEATURE:
<223> OTHER INFORMATION: antimicrobial peptide
<220> FEATURE:
<221> NAME/KEY: MOD_RES
<222> LOCATION: (21)
<223> OTHER INFORMATION: AMIDATION,

<400> SEQUENCE: 69

Lys Leu Val Arg Gln Trp Pro Ile Gly Lys Leu Val Arg Lys Leu Val
 1               5                  10                  15

Arg Lys Leu Val Arg
            20

<210> SEQ ID NO 70
<211> LENGTH: 21
<212> TYPE: PRT
<213> ORGANISM: Artificial Sequence
<220> FEATURE:
<223> OTHER INFORMATION: antimicrobial peptide
<220> FEATURE:
<221> NAME/KEY: MOD_RES
<222> LOCATION: (21)
<223> OTHER INFORMATION: AMIDATION,

<400> SEQUENCE: 70
```

```
Arg Leu Val Lys Asn Trp Pro Ile Gly Arg Leu Val Lys Arg Leu Val
 1               5                  10                 15

Lys Arg Leu Val Lys
            20

<210> SEQ ID NO 71
<211> LENGTH: 21
<212> TYPE: PRT
<213> ORGANISM: Artificial Sequence
<220> FEATURE:
<223> OTHER INFORMATION: antimicrobial peptide
<220> FEATURE:
<221> NAME/KEY: MOD_RES
<222> LOCATION: (21)
<223> OTHER INFORMATION: AMIDATION,

<400> SEQUENCE: 71

Lys Val Leu Arg Lys Val Leu Arg Lys Val Leu Arg Gln Trp Pro Ile
 1               5                  10                 15

Gly Lys Val Leu Arg
            20

<210> SEQ ID NO 72
<211> LENGTH: 21
<212> TYPE: PRT
<213> ORGANISM: Artificial Sequence
<220> FEATURE:
<223> OTHER INFORMATION: antimicrobial peptide
<220> FEATURE:
<221> NAME/KEY: MOD_RES
<222> LOCATION: (21)
<223> OTHER INFORMATION: AMIDATION,

<400> SEQUENCE: 72

Arg Val Leu Lys Arg Val Leu Lys Arg Val Leu Lys Asn Trp Pro Ile
 1               5                  10                 15

Gly Arg Val Leu Lys
            20
```